(12) United States Patent
Beger et al.

(10) Patent No.: US 11,154,287 B2
(45) Date of Patent: Oct. 26, 2021

(54) RETRACTOR HAVING A PUZZLE-TYPE CONNECTION

(71) Applicant: Aesculap AG, Tuttlingen (DE)

(72) Inventors: Jens Beger, Tuttlingen (DE); Susanne Klingseis, Biberach (DE); Christian Grimm, Tuttlingen (DE); Mario Serpa, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 184 days.

(21) Appl. No.: 16/337,737

(22) PCT Filed: Sep. 27, 2017

(86) PCT No.: PCT/EP2017/074509
§ 371 (c)(1),
(2) Date: Mar. 28, 2019

(87) PCT Pub. No.: WO2018/060253
PCT Pub. Date: Apr. 5, 2018

(65) Prior Publication Data
US 2019/0343504 A1 Nov. 14, 2019

(30) Foreign Application Priority Data
Sep. 30, 2016 (DE) .......................... 102016118605.8

(51) Int. Cl.
*A61B 17/02* (2006.01)
*A61B 17/00* (2006.01)

(52) U.S. Cl.
CPC .............................. *A61B 17/0218* (2013.01); *A61B 2017/00477* (2013.01); *A61B 2017/0225* (2013.01)

(58) Field of Classification Search
CPC ......... A61B 17/0218; A61B 2017/0225; A61F 2/88–915; A61F 2002/91591
(Continued)

(56) References Cited

U.S. PATENT DOCUMENTS

| 5,035,706 A | 7/1991 | Giantureo et al. |
| 5,383,887 A | 1/1995 | Nadal |

(Continued)

FOREIGN PATENT DOCUMENTS

| CN | 1187115 A | 7/1998 |
| CN | 102413793 A | 4/2012 |

(Continued)

OTHER PUBLICATIONS

International Search Report and Written Opinion ofr International Application No. PCT/EP2017/074509, dated Dec. 15, 2017, 8 pages.

(Continued)

*Primary Examiner* — Eduardo C Robert
*Assistant Examiner* — Tara Rose E Carter

(57) ABSTRACT

A stent retractor has a radially flexibly expandable tubular sheath divided in the peripheral direction into at least two sections, specifically a reinforcing section and an expanding section, with radial flexibilities that differ from one another, these sections being interconnected integrally. The stent retractor includes axial segments that are connected by a puzzle-type connection allowing simple separation or length adjustment in the axial direction (including when in situ) while also being made integrally, for example by a laser or water jet cutting method, preferably from a tubular blank.

20 Claims, 5 Drawing Sheets

(58) Field of Classification Search
USPC .................. 623/1.12, 1.16, 1.32; 600/206
See application file for complete search history.

(56) References Cited

U.S. PATENT DOCUMENTS

| | | | |
|---|---|---|---|
| 5,800,515 | A | 9/1998 | Nadal et al. |
| 6,017,365 | A | 1/2000 | Von Oepen |
| 6,077,297 | A | 6/2000 | Robinson et al. |
| 6,113,628 | A | 9/2000 | Borghi |
| 6,187,000 | B1 | 2/2001 | Davison et al. |
| 8,372,131 | B2 | 2/2013 | Hestad et al. |
| 8,403,978 | B2 * | 3/2013 | Schlun ............ A61F 2/91 623/1.15 |
| 2002/0087163 | A1 | 7/2002 | Dixon et al. |
| 2005/0125053 | A1 | 6/2005 | Yachia et al. |
| 2006/0173529 | A1* | 8/2006 | Blank ............ A61F 2/91 623/1.16 |
| 2006/0287706 | A1* | 12/2006 | Olsen ............ A61F 2/91 623/1.15 |
| 2007/0067012 | A1* | 3/2007 | George ............ A61F 2/915 623/1.12 |
| 2007/0219613 | A1* | 9/2007 | Kao ............ A61B 17/12022 623/1.11 |
| 2008/0195190 | A1 | 8/2008 | Bland et al. |
| 2008/0300665 | A1 | 12/2008 | Lootz et al. |
| 2009/0024203 | A1 | 1/2009 | Hestad et al. |
| 2010/0256741 | A1 | 10/2010 | Hansen |
| 2010/0312189 | A1 | 12/2010 | Shelton et al. |
| 2011/0054260 | A1 | 3/2011 | Albrecht et al. |
| 2011/0144687 | A1 | 6/2011 | Kleiner |
| 2012/0065722 | A1 | 3/2012 | Pacetti |
| 2012/0083868 | A1 | 4/2012 | Shrivastava et al. |
| 2013/0066158 | A1 | 3/2013 | Rodriguez |
| 2014/0236282 | A1 | 8/2014 | Andreas et al. |
| 2014/0288629 | A1 | 9/2014 | Amendt et al. |
| 2014/0364935 | A1 | 12/2014 | Eli et al. |
| 2016/0022448 | A1 | 1/2016 | Tobis et al. |

FOREIGN PATENT DOCUMENTS

| | | |
|---|---|---|
| CN | 103153214 A | 6/2013 |
| DE | 29708879 U1 | 7/1997 |
| DE | 10103000 A1 | 8/2002 |
| DE | 102007025921 A1 | 12/2008 |
| DE | 202011107781 U1 | 12/2011 |
| DE | 102015100933 A1 | 7/2016 |
| EP | 3181096 A1 | 6/2017 |
| JP | 03133446 A | 6/1991 |
| JP | 07265339 A | 10/1995 |
| JP | 11507567 A | 7/1999 |
| JP | 2016147049 A | 8/2016 |
| WO | 9421196 A2 | 9/1994 |
| WO | 9937245 A1 | 7/1999 |
| WO | 2013106585 A1 | 7/2013 |
| WO | 2014022094 A1 | 2/2014 |
| WO | 2014141239 A1 | 9/2014 |

OTHER PUBLICATIONS

German Search Report for German Application No. 10 2016 118 605.8, dated May 18, 2017 with translation, 12 pages.
Non Final Office Action for U.S. Appl. No. 14/997,839, dated Feb. 5, 2020, 19 pages.
Chinese Office Action for Chinese Application No. 201610044869.5, dated Jul. 31, 2019, with translation, 18 pages.
Japanese Notification of Reason for Rejection for Japanese Application No. 2016-010829, dated Dec. 3, 2019 with translation, 6 pages.
Chinese Office Action received in Application No. 201780060843.2 dated Nov. 2, 2020, 13 pages.
Chinese Search Report received in Application No. 2017800608432 dated Oct. 20, 2020, 3 pages.
German Search Report dated Nov. 4, 2015 for German Application No. 10 2015 100 932.3, 13 pages.
Roche Lexikon Medizin, 5. Auflage, Urban & Fischer 2003, Definition: "Distraktor", "Sten" and "Wundsperrer," 3 pages.
Office Action received in Japanese Office Action dated Aug. 10, 2021, with translation, 8 pages.

* cited by examiner

RETRACTOR HAVING A PUZZLE-TYPE CONNECTION

RELATED APPLICATIONS

This application is the national phase entry of International Application No. PCT/EP2017/074509, filed Sep. 27, 2017, which claims the benefit of priority from German Application No. 10 2016 118 605.8, filed Sep. 30, 2016. The contents of International Application No. PCT/EP2017/074509 and German Application No. 10 2016 118 605.8 are incorporated by reference herein in their entireties.

FIELD

The present invention relates to a stent retractor or retractor stent and in particular to a single-use retractor stent whose segmental construction allows individual length adjustment (in the axial direction).

BACKGROUND

A retractor is generally a surgical instrument/component for keeping open an operation field/incision or expanding it. This instrument/component is inserted into the surgical field from outside the patient and the expansion elements are spaced apart. As a result, connective and/or muscle tissue is pressed apart (radially) and hence the surgical field is expanded. The required extension forces are applied either extracorporeally via holding arms, if necessary mounted on the operating table, or intracorporally by spring and/or support elements, which apply force to the spreading elements.

For example, U.S. Pat. No. 6,187,000 B1 discloses a retractor of this kind with an expandable distal end. Here, a sort of foil made of stainless metal is rolled up into a tube/funnel, with the adjoining or overlapping foil edges being riveted to each other. A first, axially end-side rivet forms a swivel hinge, whereas a second, axially spaced end-side rivet is guided in a slot which is formed in the foil and, when the foil is rolled up, extends over the full circumference, in order to increase or reduce the diameter of the foil roll in portions while pivoting around the first rivet. This allows a cylinder and a funnel shape to be formed.

Another construction for a stent retractor of the present kind is known from U.S. Pat. No. 8,372,131 B1. This construction provides for the arrangement of a stent tube or hose, consisting of a material processed into a homogeneous wire mesh, preferably with memory properties, whereby the inner and/or outer side of the wire mesh is covered with a fluid-tight membrane, for example made of PTFE. The stent tube is initially mounted on a dilatation set consisting of a trocar shaft surrounded by a dilatation balloon and having at its distal end a kind of bone anchor in the form of a single, centrally located nail or bone screw.

For intracorporeal placement of the known stent retractor, the trocar shaft is inserted into the patient's body and anchored to a patient's bone (e.g. vertebral bone) using the nail or screw. The dilatation balloon is then inflated, causing the stent retractor to widen radially, pressing the surrounding patient tissue evenly apart in radial direction. After loosening the bone anchor and retracting the trocar shaft while leaving behind the expanded stent retractor, a patient access with an access diameter is created to perform an operation, preferably with minimally invasive surgical instruments, which can be inserted into the channel defined by the stent retractor.

From WO 2014/022094 A1 a textile structure with separate support elements to form a retraction device is generally known. According to this, a braided tissue formed into a tube is pressed radially outwards by means of a sort of separate support frame in order to apply an expanding force to the surrounding patient tissue. The supporting frame also has a number of rods penetrating the braided tissue radially outwards, which temporarily anchor themselves in the patient tissue and thus axially retain the structure in the patient's body.

Finally, US 20100312189 A1 discloses a retractor in which several folds or beads of different lengths (and thus sections of different radial flexibility) are connected to one another and produced so as to partially overlap in a wall of a tubular element, by means of which the tubular element can be expanded and contracted.

However, it has turned out with said retractor systems that they have a large number of components on the whole and are therefore relatively expensive to manufacture. This is why they cannot be used as disposable articles or only to a limited extent. This results in a high expenditure of time and high costs for the reconditioning of standard tractor systems.

In addition, the known prior art solutions are not individually adaptable or able to be adjusted in length, which requires a large number of different components in order to be prepared for different applications.

A stent with retractor function is known from DE 10 2015 100 933, comprising a radially flexible expandable sheath that is subdivided in the peripheral direction into at least two integrally fabricated sections of different radial flexibility and which has several axial segments that are connected in an integrally bonded manner via predetermined breaking points and can be separated. In this way, such a stent retractor can be flexibly adjusted in its length and adapted in situ.

However, such a solution in which the axial segments are connected exclusively via predetermined breaking points, has proved to be unfavorable, since in order to achieve sufficient stability during an operation and reliably prevent unintentional buckling or bulging of the stent, the predetermined breaking points must be designed to be comparatively massive, which in turn increases the forces required for separation and in some cases requires special tools for adjusting the length of the stent in situ. Too much force applied to the stent during cutting in situ can also cause trauma to the tissue surrounding the stent. In addition, sharp-edged fracture edges may occur at the predetermined breaking points, which pose a risk of injury.

The invention described below is based on the stent with the retractor function just described, but makes it a preferred task to develop a new connection and separation concept that allows a simpler, preferably burr-free, in situ separation of the axial segments with the same stability of the connection elements as the solutions known in prior art and at the same time reduces the risk of trauma in the patient by such a separation.

SUMMARY

In view of the above state of the art, the object of the present invention is to provide a generic stent (retractor) that is suitable or designed as a disposable article (single-use concept).

Furthermore, a preferred objective of the present invention is to provide a retractor system that can be theoretically shaped and adapted (round, oval, etc.) as desired, especially for minimally invasive accesses (e.g. lumbar, thoracic and cervical spinal accesses, cranial applications), which is also preferably easy to adjust in length, especially in-situ, after insertion of the retractor.

Moreover, this invention makes it a preferred task that the retractor can be adjusted in its length with comparatively little effort using the simplest tools (e.g. clamps, pliers) or also by hand and yet without any risk of injury from burrs or cutting edges.

Finally, another preferred goal of this invention is that the stent is produced as a one-piece connection during the manufacturing process or can be manufactured from a blank without the need of any assembly process.

The core idea of the invention is therefore to divide the stent retractor into a number of axial/longitudinal segments (i.e. segments that can be separated from one another in the axial direction) on which undercuts that protrude/recede in the axial direction and act at least in the axial direction are integrally formed and can be fitted into one another according to the puzzle piece principle.

Puzzle pieces are generally flat elements that are contoured at their edges with protrusions and recesses, preferably made of a cardboard material, which can be firmly connected to one another by putting the protrusions and recesses together. Preferably the puzzle pieces have head-like protrusions as well as bay-like (horseshoe-shaped) recesses which interact with each other in such a way that the connected puzzle pieces can no longer be torn apart.

The invention makes use of this connection principle by forming corresponding contours on the front edges of the preferably sheet or lamella-like (thin-walled) stent or retractor segments to form quasi three-dimensional puzzle pieces whose protrusions and recesses fit into one another (without an integral connection) in order to hold the segments detachably together in the axial direction. If the segments are then to be separated from each other again, the cooperating protrusions and recesses only have to be pressed apart perpendicular to the axial direction of the stent, without this resulting in a breaking edge.

In order to avoid unintentional loosening of the segment connection according to the puzzle piece principle, the protrusions and recesses at the rim or edge can preferably be chamfered/beveled in opposite directions. This means that the rims/edges of the contours forming the protrusions and recesses are beveled relative to each other in such a way that displacement of two segments perpendicular to the axial direction of the stent is blocked by the oppositely oriented and thus oppositely acting chamfers of two radially opposed protrusion-recess connections. In other words, the edges of two radially opposed protrusion-recess connections are chamfered radially inwards (tapered radially inwards), thereby blocking radial displacement of two coupled segments.

Alternatively, however, it may also be provided that two radially opposed protrusion-recess connections (these are required at least for the axial locking of two adjacent segments) are not exactly 180° opposite each other and thus get entangled when the two segments coupled to each other are shifted sideways. Finally, it can be alternatively provided that at least three protrusion-recess connections are provided, which are formed at the segments at a preferably equal circumferential distance.

More specifically, according to a first aspect of the present invention, a stent adapted for use as a retractor is proposed. For this purpose, the stent has a radially flexible, expandable, tubular wall structure, which is divided into at least two sections with different (radial) flexibility when viewed in the peripheral direction. The sections of higher flexibility or expanding sections serve to make it possible to change the diameter of the stent and thus give the stent the ability to be deformed/expanded as desired in the radial direction (e.g. round, oval, etc.), whereas the sections of lower flexibility or the reinforcement sections increase the stent's stability against external radial forces at least in certain radial directions and thus help to maintain sufficient stiffness for the stent to hold the tissue in the distended state. The preferably integral design of the stent (individual stent segments) represents a quick and easy method of production, for example by laser or water jet cutting of metal sheets. This allows an economic and practical implementation of a single-use concept.

According to the invention, the stent is divided in the axial direction into at least two separable segments (longitudinal segments), each of which is coupled to the other by at least one connecting element/connecting unit (protrusion-recess connection). At least one of these connecting elements is formed as a puzzle-type connection/linking, which is distinguished structurally/constructionally by the fact that a first axial segment has at least one recess or a concave puzzle section in which an inserted section/partial surface or a convex puzzle section of a second, adjacent axial segment is inserted and the two corresponding puzzle sections are held together by positive locking in the axial and peripheral directions, but can be separated from one another in the radial direction.

It could also be said that the course of an intersection line or separating edge (interface) between two adjacent stent segments to be interconnected forms at least one undercut site through which the adjacent segments are interconnected both in the axial direction and in the peripheral direction by positive locking, but can be detached by a radial relative movement of the two segments relative to each other locally in the area of the undercut site.

Due to the curvature of the tubular wall structure of the stent, such a puzzle-type connection, especially if two or more such connecting sections are present, can cause self-locking, since the puzzle-type connections can only be separated locally in the radial direction and these local radial directions can be angled relative to each other, as described above. This can lead to a segment to be separated only being detachable by an elastic and/or plastic deformation of the stent and/or by repeatedly moving the segments back and forth relative to each other. Axial and torsional forces acting on the stent, on the other hand, can be fully transmitted by the positive fit formed by the puzzle-type connection, which can be particularly important for the stability of the stent when it is inserted into an operating field and/or when an operation site is kept open. Such a puzzle-type connection font's a positive connection between two segments using the curvature of the stent, which offers a high stability of the connection point with comparatively easy detachability, since the individual puzzle-type connections can be easily separated by a local radial movement (movement in a preferred direction) at the connection point. In this way, a simple separation concept for flexible length adaptation of the stent by hand or with the simplest tools can be implemented.

In contrast to predetermined breaking points or integral connections, which are the most common solution known in the state of the art for separable connecting elements in components manufactured in one piece, the strength and stiffness of the connection are not proportional to the material thickness with a puzzle-type connection according to the invention. If a higher stiffness or strength is to be achieved in a predetermined breaking point, the diameter of the predetermined breaking point must be increased and thus also the force is increased that must be applied to separate the integral connection. From a certain material thickness of the predetermined breaking point, it may even be necessary to use a cutting tool to separate the integrally bonded connection. A puzzle-type connection according to the invention, on the other hand, has the advantage that the segments connected in this way can be separated more easily with the same or higher transferable loads, without special separating tools. In addition, there is a risk that sharp edges or burrs may form when integrally bonded connections are cut off, which can no longer be deburred in situ and represent a risk of injury for patient and user, which is not the case with a puzzle structure according to the invention.

According to a preferred embodiment, the recess and the inserted section may be symmetrical and the inserted section may preferably narrow proximally or form a bottle neck to create a positive fit in the axial direction. Such an adapted recess together with the corresponding inserted section could also be referred to as a tongue-and-groove connection-like design, since such a connecting element e.g. in the cross-sectional form of a classic puzzle-type connection, can be designed to be dovetail-shaped, or especially preferred in the form of a T-slot and tongue connection.

According to another preferred embodiment, the cutting edges can be directed radially to the axis of rotation along at least one puzzle-type connection. The term "cutting edge" generally refers to the lateral edge surfaces of all (partial) surfaces formed in the tubular lateral surface of the stent. Such an alignment of the cutting edges to the axis of rotation has the consequence that the cutting edges are not arranged parallel or obliquely to each other, allowing a simpler production, since e.g. with laser beam cutting the laser beam can always be directed to the axis of rotation as standard.

Preferably, the gap widths between the cutting edges can be chosen to be relatively small compared to the tube wall thickness, so that an undercut in radial direction can be created by the setting angle of the cutting edges, by means of which the segments of the stent in the area of the puzzle-type connection can only be separated by a relative radial movement, in which the inserted section of the puzzle-type connection, relative to the partial surfaces adjacent in peripheral direction, is guided radially outwards. In other words, only a separation in a preferred direction is possible with this embodiment. Such an orientation of the cutting edges makes an unintentional loosening of the puzzle-type connection less likely. The size of the resulting undercut can be adjusted via the gap width between the cutting edges and the wall thickness of the stent. The gap widths are preferably chosen to be relatively small (approx. 0.01 mm to 0.1 mm, preferably approx. 0.05 mm) in order to be able to create a sufficient undercut even with comparatively small wall thicknesses (approx. 0.5 mm to 1.2 mm, preferably 0.7 mm to 1 mm), which can still be loosened manually.

In order to achieve a further increase in stability, the cutting edges within a puzzle-type connection can be designed according to a further embodiment with at least one puzzle-type connection such that counteracting surfaces are created which must be moved in opposite directions to release them. It is preferable to have different undercuts on partial surfaces in pairs on a puzzle. For example, a part of the cutting edges along the puzzle-type connection can only be released by a radial inward movement, while the remaining cutting edges can only be released by radial outward movement. Such an embodiment further inhibits a loosening of the puzzle-type connection, since the individual puzzle-type connection can only be released by an elastic or plastic deformation of the puzzle elements to overcome the radial undercuts formed by the cutting edges.

According to one embodiment of the invention, a puzzle-type connection may also be designed in such a way that the partial surfaces of two adjacent segments in the peripheral direction engage/protrude alternately into the lateral surface of the respective other segment and in this way create counteracting surfaces, whereby the cutting edges can nevertheless all be directed towards the axis of rotation of the stent, which facilitates easier fabrication.

According to a preferred embodiment of the invention, at least one puzzle-type connection may be designed such that the proximal constriction of the inserted section is produced by two hook-shaped elements formed at the distal edges of the recess, which in turn project into the surface of the second segment having the inserted section, and thus, even when the cutting edges are directed to the axis of rotation, produce counteracting surfaces in accordance with the embodiment described above, and thus a self-locking effect.

According to a further embodiment, the puzzle-type connection can be combined with an integrally bonded connection/predetermined breaking point, i.e. the cut line along the puzzle-type connection can be integrally bridged at least at one point by a web to further stabilize the connecting element and prevent unintentional tilting of the puzzle-type connection. Here, the web (predetermined breaking point) can be selected to be relatively small, e.g. with a diameter/web width of 0.01 mm to 0.1 mm, preferably approx. 0.05 mm, to simplify break-off/separation of the predetermined breaking point.

Thus, different types of puzzle-type connection are proposed, which depending on the requirements of the application can increase the stability of the connection by adding counteracting undercuts and/or predetermined breaking points to the original puzzle-type connection, as required.

According to another embodiment of the invention, the retractor stent may have a longer continuous segment at its distal end in the axial direction and a number of shorter separable segments at its proximal end. For the distal long segment, which is first inserted into the surgical site, a higher strength and/or rigidity can be achieved due to the axial continuousness, while those proximal segments that protrude from the surgical site after insertion of the stent retractor can be simply separated in order to shorten the stent retractor to an appropriate length or to adapt its length flexibly.

According to a preferred embodiment, the stent may have at least two connecting elements per segment, which may be diametrically opposed or circumferentially evenly distributed to ensure an even flow of force and minimize the risk of unwanted buckling when applying an axial load, which could result in injury to the patient and/or the user.

According to a preferred design of the invention, provision is made that the expanding sections each consist of a number of axially spaced, preferably elastic or plastically deformable expansion elements, which are each preferably formed of an accordion wire extending in the peripheral direction. This allows the wall structure of the stent to be produced by punching or cutting, preferably laser or water jet cutting, for example from a (closed) tube profile, both in the area of the expanding sections and in the area of the reinforcing sections and the puzzle-type connections, which can also be subsequently deburred. Thus, production is simple and cost-effective and therefore suitable for single-use products.

BRIEF DESCRIPTION OF THE DRAWING FIGURES

The invention is explained in more detail below using preferred exemplary embodiments with reference to the accompanying Figures in which.

DETAILED DESCRIPTION

Figure 1:
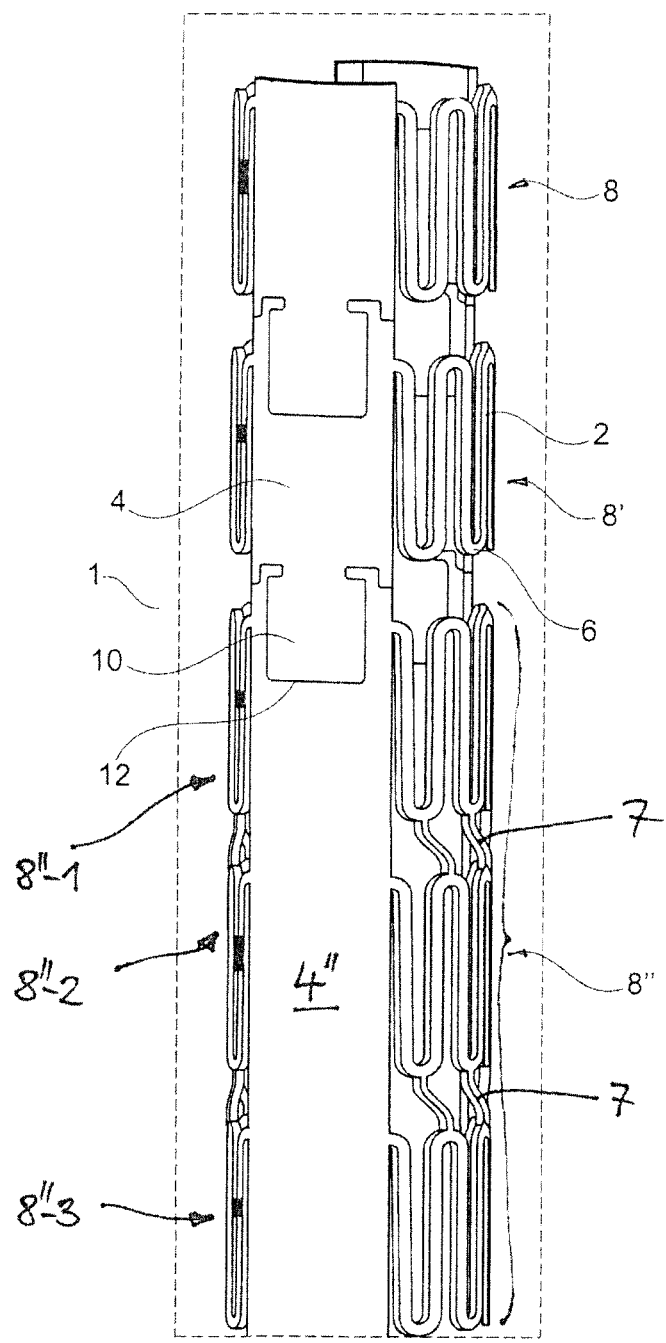
FIG. 1 is a representation of a stent according to a first preferred exemplary embodiment of the present invention.

According to FIGS. 1 to 5, the wall structure of a stent (retractor) 1 according to a first preferred exemplary embodiment of the present invention consists of two peripheral sections 2 with low stiffness as seen in the peripheral direction (hereinafter referred to as expanding sections/elements) and two peripheral sections 4 with comparatively high stiffness (hereinafter referred to as reinforcing sections/elements) which are arranged in the peripheral direction alternately with respect to one another and linearly in the axial direction.

In principle, the stent 1 according to the invention has a tube or hose shape, with the peripheral sections of identical or similar stiffness being diametrically opposed to each other. The stent 1 is also integrally fabricated, i.e. the individual peripheral sections are integrally bonded.

The comparatively thin-walled stent tube (approx. 0.5 to 1.5 mm) is preferably divided into the above-mentioned peripheral sections by laser cutting or water jet cutting. However, it should be noted that other processing techniques such as punching or milling can also be used to produce the wall structure described below. Depending on requirements and intended purpose/application site, the initial diameter (inner diameter of the stent tube in the constructional position, i.e. when not expanded) can be in a range of 10-30 mm, for example.

The stent 1 essentially has a wall structure at its expanding sections 2 which is basically taken over from a standard vessel stent, such as a stent marketed by B Braun under the registered trademark COROFLEX®. This means that the stent 1 is formed at least in the region of its expanding sections (expansion elements) 2 from a number of axially spaced, preferably parallel bands 6, which extend in a serpentine or concertina-shaped manner in the peripheral direction and thus form flexible expansion reserves in the radial direction in the region of their concertina shape.

In order to increase the stability, the stiffer peripheral sections (reinforcing sections) 4 are arranged between the two expanding sections 2 (alternately) when viewed in the peripheral direction. The reinforcing sections (reinforcing elements) 4 are formed by essentially closed, preferably rectangular plate sections which, in their basic form and as seen in the axial direction, are curved like a trough or tray and are channel-shaped and are intended not to widen radially or only to a slight extent.

As can also be seen from FIGS. 1 to 5, the stent/retractor 1 according to the invention consists of several axially spaced/separate (circular/ring) segments 8, 8', 8", which also each consist of the four peripheral sections as described above, the circular segments 8 being connected to one another via the reinforcing sections 4 by means of connecting elements 10 (not integrally). This segmental design has the advantage that when the stent diameter is radially expanded, its axial length remains essentially the same, since only the individual segments 8, 8', 8" are radially expanded. Furthermore, the connecting elements 10 can be easily removed by hand or with the simplest tools, e.g. pliers or clamps, so that an intra-operative length adjustment of the stent 1 is possible.

Figure 6:
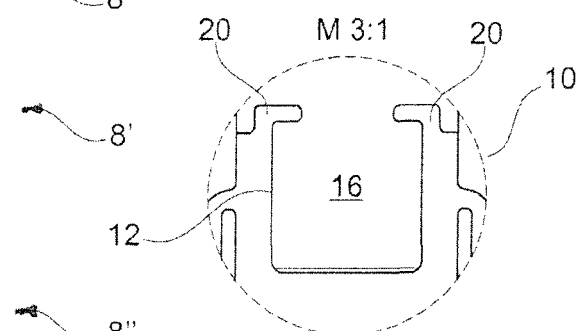
FIG. 6 shows a detail of the puzzle-type connection according to the first preferred embodiment.

As shown in FIG. 6, the connecting elements 10 are formed by a recess/cutout 18 arranged at an axial edge (front edge) of a first segment 8' and a corresponding inserted section/protrusion 16 of an adjacent second segment 8. In this exemplary embodiment, the recess is essentially rectangular and preferably has two hook-shaped partial surfaces/sections 20 at its distal lateral edges, which create a positive fit with the inserted section 16 in the axial direction. By means of these connection elements 10 in the form of a puzzle-type connection, a form fit of the two adjacent segments in the axial and the peripheral direction is produced, while the connection remains detachable by a movement of the inserted section 16 in the radial direction.

Figure 3:
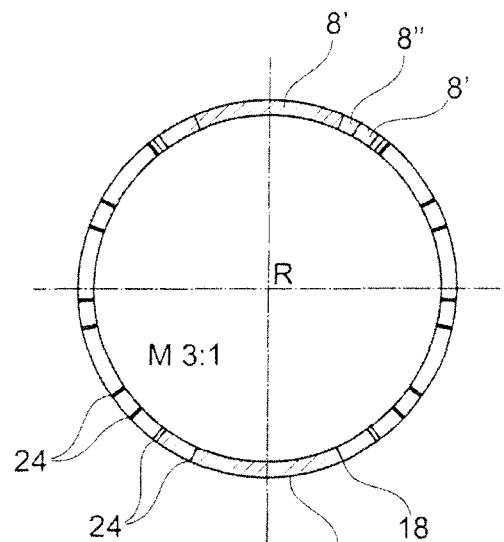
FIG. 3 is a sectional view through a stent according to the first preferred embodiment.
Figure 4:
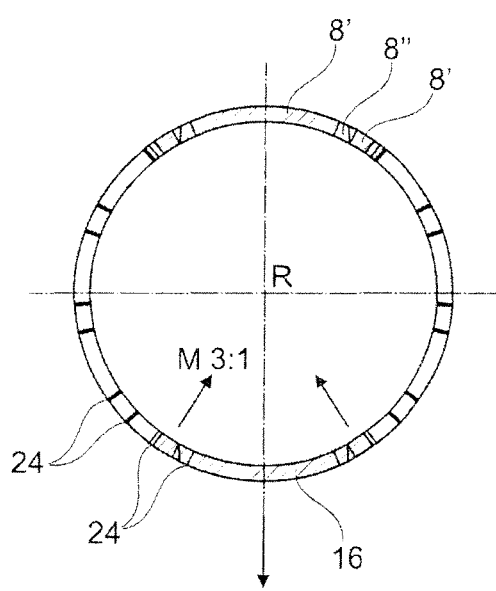
FIG. 4 shows another sectional view through a stent according to the first preferred embodiment.

As shown in particular in the cross-sectional views according to FIGS. 3 and 4, the radial cutting edges in the protrusion/set-back section of the stent are oriented to the rotational axis R and aligned therein. As a result, the radial cutting edges 24 of each protrusion/set-back section, which are spaced apart in the peripheral direction, are set obliquely relative to each other and, with a suitably selected ratio of gap width to wall thickness, form radially acting undercuts, so that certain sections can only be detached in a defined preferential direction (radial direction inwards) (indicated by arrows). Due to the fact that the hook-shaped partial surfaces 20 of the first segment 8' project into the area of the second segment 8 or are received by complementary hook-shaped recesses in the second segment 8, the situation arises that, around the hook-shaped partial surface 20, counteracting radial undercuts 14, 14' form at the cutting edges 24 of the second segment 8 (see FIG. 4); therefore, the latter can only be released from the puzzle-type connection by overcoming these radial undercuts 14, 14' by plastic and/or elastic deformation of the material in this area, which is possible with little effort with corresponding wall thicknesses of about 0.7 mm to 1 mm.

Figure 2:
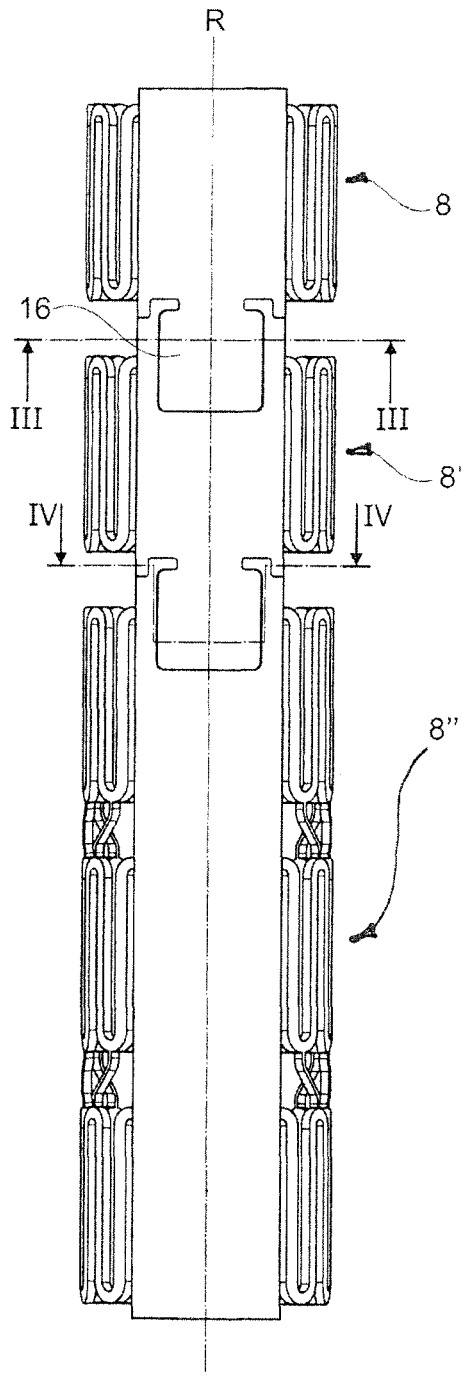
FIG. 2 is a side view of the same embodiment.
Figure 5:
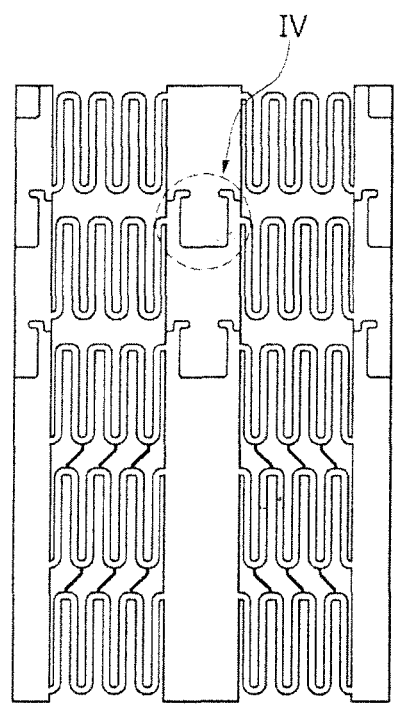
FIG. 5 shows a flat pattern of a wall structure according to the first preferred embodiment.

FIGS. 1, 2 and 5 show that a stent according to the invention having a retractor function can be constructed in accordance with one embodiment such that it can have a longer axial segment 8" at its distal end, which is inserted into the patient first, in which several serpentine expanding bands 6 in the segment sections 8"-1, 8"-2 and 8"-3 can be connected in a integrally bonded manner in the axial direction via S-shaped connecting sections 7 and serve as an expanding section 2 when connected in series in a segment 8". This gives the distal segment 8", in combination with a continuous reinforcing section 4", a higher stability compared to the shorter segments 8, 8' which are detachably connected/coupled via puzzle-type connection elements 10, which may be useful since the distal section can be exposed to higher forces during insertion into the surgical site and in situ only those proximal segments have to be separated which ultimately protrude from the surgical site.

For use, the stent with 1 according to the invention with retractor function can be inserted into an operation site e.g. with the aid of a trocar and, after removal of the trocar, is able to keep open an access to the operation site. The individual segments 8, 8', 8" of the stent 1 can be expanded individually. After expansion, proximally protruding segments 8, 8', 8" of the stent 1 can be separated with simple means and little effort and the stent 1 can be brought to a suitable length.

Figure 7:
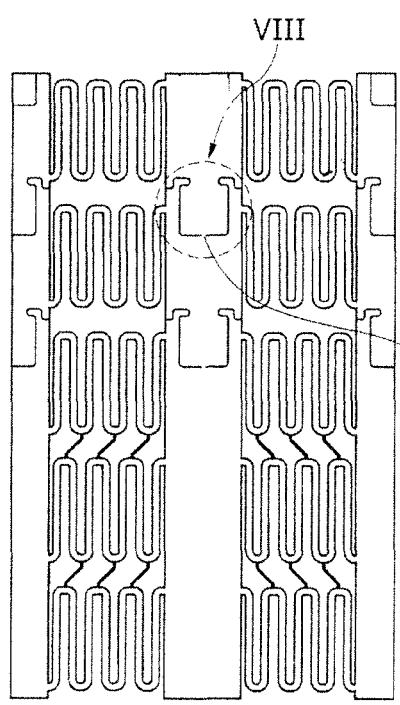
FIG. 7 shows a flat pattern of a wall structure according to a second preferred embodiment.
Figure 8:
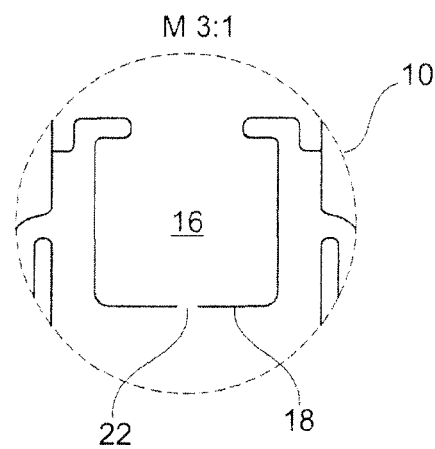
FIG. 8 shows a detail of the puzzle-type connection according to the second preferred embodiment.
Figure 9:
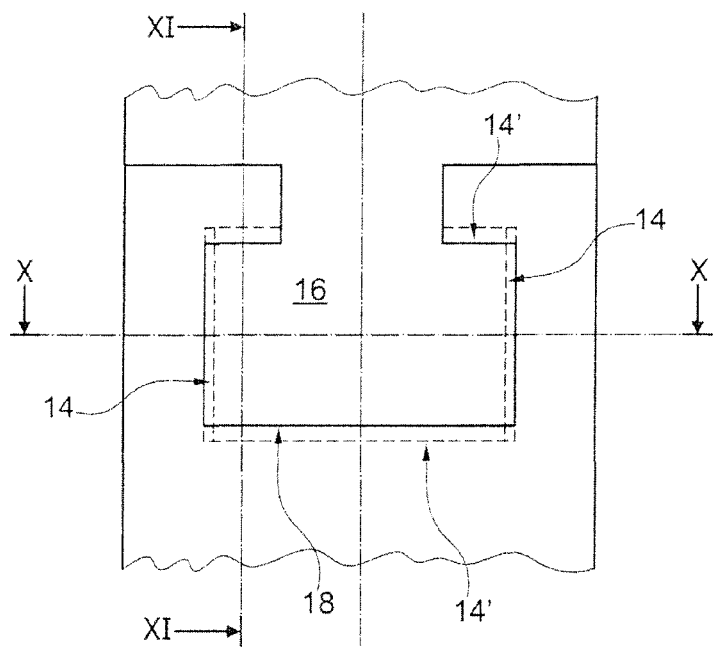
FIG. 9 shows a detail of a puzzle-type connection according to a third embodiment with counteracting undercuts.
Figure 10:
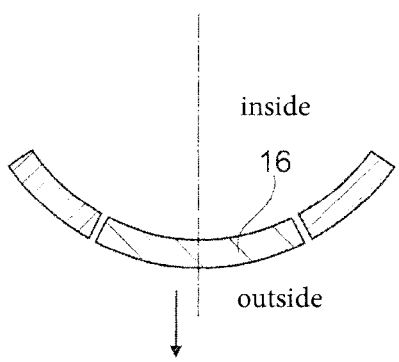
FIG. 10 is a sectional view through a puzzle-type connection according to a third embodiment.
Figure 11:
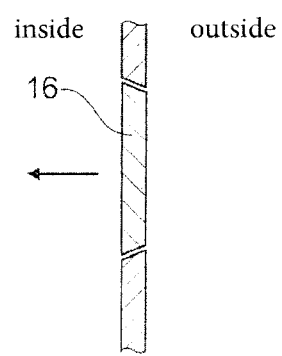
FIG. 11 is another sectional view through a puzzle-type connection according to the third embodiment.

According to another embodiment shown in FIGS. 7 and 8, a connecting element 10, in addition to the puzzle-type connection described above, may have an integrally bonded predetermined breaking point 22 between the recess 18 and the inserted section 16, which bridges the separation line 12 between the sections 8, 8' like a web or bridge, so to speak. In this way, an even higher stability of the connection can be achieved, whereby the connection, taking advantage of the preferential direction established by the puzzle-type connection, can be separated more easily by hand than a purely integrally bonded connection per predetermined breaking point with similar stability. The predetermined breaking point 22 can, for example, be designed with a diameter of 0.01 mm to 0.1 mm, preferably approximately 0.05 mm.

According to further embodiments shown in FIGS. 9 to 13, additional counteracting axial undercuts 14, 14' can also be produced at the cutting edges by selectively controlling the cutting beam/separating tool. Thus, for example, the axially extending cutting edges 24 can be set relative to each other along a puzzle-type connection in such a way that an inserted section 16 can only be released radially outwards (FIG. 10), while the cutting edges 24 are set relative to each other in the peripheral direction in such a way that the inserted section 16 can only be released radially inwards (FIG. 11), whereby the undercuts 14, 14' inhibit each other and additionally stabilize the connection. The inserted section 16 can therefore only be released from the puzzle-type connection by elastic or plastic deformation in such an embodiment. The cross-sectional views also clearly show that the radial undercuts form essentially wedge-shaped undercuts due to the edges angled relative to each other.

Figure 12:
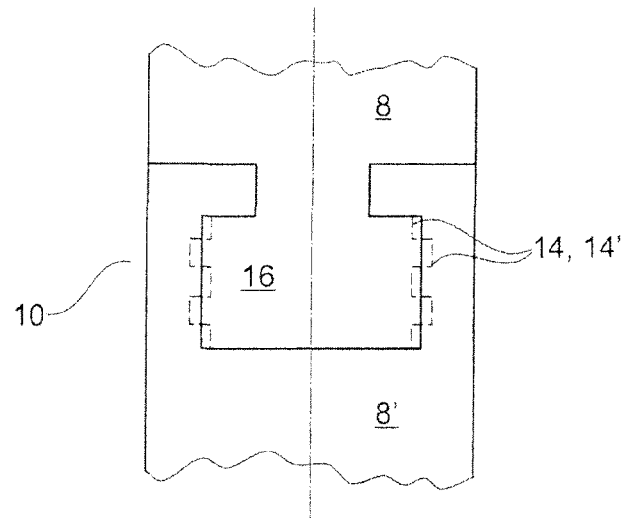
FIG. 12 shows a detail of a puzzle-type connection according to a fourth embodiment with counteracting undercuts.
Figure 13:
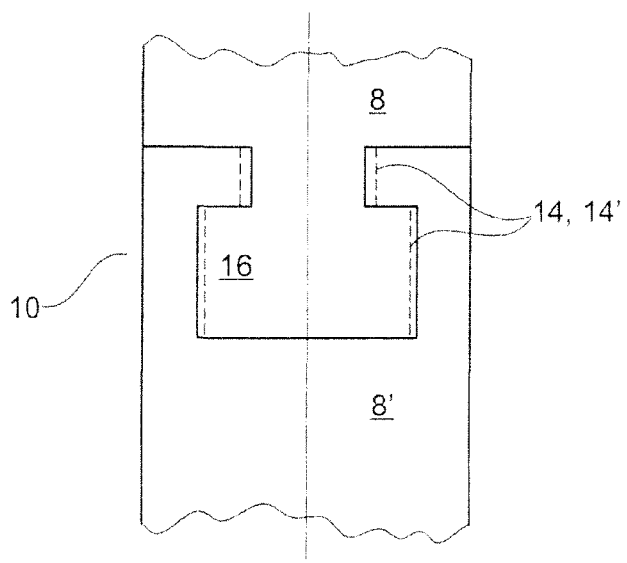
FIG. 13 shows a detail of a puzzle-type connection according to the fourth embodiment with counteracting undercuts.

As shown in FIG. 12, the alignment of the radial undercuts 14, 14' can also be varied/alternated along an individual cutting edge section in order to create a self-locking effect. Similarly, parallel cutting edge sections along the recess 18 can also inhibit each other, preferably in pairs (see FIG. 13). Any combination of the above-mentioned cutting edge orientations is also conceivable to create stabilizing undercuts.

The stent 1 can be destroyed to remove it. It may also be reduced in size by simply pressing it together, and then it can be removed. Especially in case that a (distally) funnel-shaped structure was created during the expansion process, it is conceivable that, for example, the stent 1 will be compressed again by a compression forceps which engages in the stent structure.

Steel, titanium or plastic can be used as the material for the stent 1 according to the invention, whereby a plastic part is preferably produced by injection molding. Furthermore, the stent 1 can be deburred after cutting the wall profiles, for example by electropolishing. In addition, the surface of the remaining structures can also be matted or coated to improve the photometric reflection properties, for example under microscope applications.

In summary, the invention suggests a stent with the following properties:
Single-use stent (retractor) 1, which can be shaped and adapted as desired;
segmental construction allows individual length adjustment;
during the manufacturing process, a one-piece connection is created by laser cutting;
individual segments 8, 8', 8" are held in a form-fit manner by puzzle-type connections using the curvature of the stent 1;
radial undercuts are created at the cutting edges along the puzzle-type connections, which prevent any unintentional detachment of the puzzle-type connections; and
the puzzle-type connection concept may also be combined with predetermined breaking points.

These properties have the following advantages:
Simple segmental separation of the retractor, also in-situ;
the length of stent 1 does not have to be determined before insertion;
the segments can also be separated after the retractor has been expanded, as the undercuts provide the necessary strength;
easy detachment with high stability of the puzzle-type connection at the same time;
the connection is made during the manufacturing process—no assembly is required; and
simple instruments such as clamps or pliers can be used for separation.

Based on the exemplary embodiment shown, the holding device 1 according to the invention can be modified in many respects.

By way of example, the expanding sections may take a variety of shapes and do not necessarily have to be strip-shaped but can also be grid or honeycomb-shaped or formed as a thin-walled closed sheet with a folding structure, for example.

It is also possible to combine the stent described with other state-of-the-art retractor components and functions, such as a sheath, preferably made of plastic foil, for tissue protection or with devices for temporarily anchoring the retractor stent to the patient.

The invention claimed is:

1. A stent with retractor function, comprising:
a tubular sheath that is flexibly expandable in a radial direction and that is divided in its circumferential/peripheral direction into at least a first section of higher radial flexibility and a second section of lower radial flexibility, the first section of higher radial flexibility directly adjoined to the second section of lower radial flexibility in the circumferential/peripheral direction,
the first section of higher radial flexibility forming an expansion section of the tubular sheath; and
the second section of lower radial flexibility forming a reinforcement section of the tubular sheath,
the stent further divided in an axial direction into a plurality of segments,
each segment having a reinforcing section and an expanding section, the plurality of segments coupled at their respective reinforcing sections via axial connecting sections which form nominal separation points for segmental length shortening, at least one axial connecting section being a jigsaw-puzzle connecting section arranged between two adjacent reinforcing sections of two segments, the jigsaw-puzzle connecting section being formed by at least one axially oriented recess in a first segment of the plurality of segments and at least one corresponding inserted section or axially oriented protrusion of a second segment of the plurality of segments that is adjacent to the first segment, the at least one corresponding inserted section or axially oriented protrusion fitted in the at least one axially oriented recess, the first and second segments each forming an axially acting undercut engagement by which the first and second segments are positively connected to one another in the axial direction and the circumferential/peripheral direction, but are configured to be separated by a radial relative movement of the first and second segments at the undercut engagement.

2. The stent with retractor function according to claim 1, wherein the expanding section and the reinforcing section are arranged alternatingly in the circumferential/peripheral direction and are aligned in the circumferential/peripheral direction.

3. The stent with retractor function according to claim 2, wherein the expansion section comprises at least two expansion sections with higher radial flexibility and wherein the reinforcement section comprises at least two reinforcement sections with lower radial flexibility, the sheath comprising a perimeter and being divided into the at least two expansion sections and the at least two reinforcement sections along its perimeter.

4. The stent with retractor function according to claim 3, wherein the at least two expansion sections each comprise a plurality of spaced bands and the at least two reinforcement sections each comprise a solid sheet structure.

5. The stent with retractor function according to claim 4, wherein the jigsaw-puzzle connecting section is formed integrally in one of the at least two reinforcement sections.

6. The stent with retractor function according to claim 5, wherein the jigsaw-puzzle connecting section is cut into the solid sheet structure by laser or water jet cutting of a separation line into a tubular blank.

7. The stent with retractor function according to claim 6, wherein the separation line has a gap width of 0.01 mm to 0.1 mm, and the tubular sheath has a wall thickness of 0.5 mm to 1.2 mm.

8. The stent with retractor function according to claim 6, wherein the at least one corresponding inserted section or axially oriented protrusion is symmetrical and forms a constriction/narrowing which defines an undercut acting in the axial direction, and the at least one axially oriented recess is complementary thereto.

9. The stent with retractor function according to claim 8, wherein the first and second segments comprise radial cutting edges along the separation line between the at least one axially oriented recess and the at least one corresponding inserted section or axially oriented protrusion, the radial cutting edges being directed radially onto an axis of rotation of the stent and set obliquely relative to each other so as to form a radially acting undercut, whereby the at least one corresponding inserted section or axially oriented protrusion is configured to only be released radially outwardly from the at least one axially oriented recess by a local relative movement.

10. The stent with retractor function according to claim 9, wherein the radial cutting edges are adapted so as to form radially counteracting undercuts configured to only be released in opposite directions, whereby the at least one corresponding inserted section or axially oriented protrusion is configured to only be released by a plastic and/or elastic deformation in one direction.

11. The stent with retractor function according to claim 10, wherein the radially counteracting undercuts are produced by hook-shaped partial surfaces formed on the first segment at distal edges of the at least one axially oriented recess, which project into a lateral surface of the second segment.

12. The stent with retractor function according to claim 9, wherein the separation line of the jigsaw-puzzle connecting section is bridged by a web at at least one point in an integrally bonded manner, the web serving as a predetermined breaking point.

13. The stent with retractor function according to claim 1, wherein the plurality of segments comprises a distal segment arranged at a distal end of the stent and having a first axial length, and one or more proximal segments located proximally to the distal segment, each of the one or more proximal segments having a second axial length, the first axial length being longer than the second axial length.

14. The stent with retractor function according to claim 1, wherein at least two connecting elements are formed on at least one of the plurality of segments, the at least two connecting elements diametrically opposed or evenly spaced in the circumferential/peripheral direction.

15. The stent with retractor function according to claim 1, wherein the expansion section and the reinforcement section are produced by laser or water jet cutting of a tubular blank.

16. The stent with retractor function according to claim 1, wherein the reinforcing sections of two adjacent segments are linearly aligned along a straight line relative to one another in the axial direction.

17. A retractor comprising:
a tubular sheath having a perimeter, the tubular sheath being flexibly expandable in a radial direction, the tubular sheath further being divided along its perimeter into at least a first section of higher radial flexibility and a second section of lower radial flexibility, which are integrally interconnected in a circumferential/peripheral direction to form a ring,
the first section of higher radial flexibility comprising a plurality of spaced bands and forming an expansion section of the tubular sheath; and
the second section of lower radial flexibility comprising a solid sheet structure and forming a reinforcement section of the tubular sheath,
the retractor further divided in its axial direction into a plurality of segments,
each segment having at least one reinforcing section and at least one expanding section;
the segments being coupled via axial connecting sections which form nominal separation points for segmental length shortening,
at least one of the axial connecting sections being formed by at least one axially oriented recess in a first segment of the plurality of segments and at least one corresponding inserted section or axially oriented protrusion of a second segment of the plurality of segments that is adjacent to the first segment of the plurality of segments, the at least one corresponding inserted section or axially oriented protrusion fitted in the at least one axially oriented recess such that the at least one axially oriented recess and the at least one corresponding inserted section or axially oriented protrusion form an interlocking connection.

18. A stent with retractor function, comprising:
a tubular sheath that is flexibly expandable in a radial direction and that is divided in its circumferential/peripheral direction into at least a first section of higher radial flexibility and a second section of lower radial flexibility, which are integrally interconnected,
the first section of higher radial flexibility forming an expansion section of the tubular sheath; and
the second section of lower radial flexibility forming a reinforcement section of the tubular sheath,
the stent further divided in an axial direction into a plurality of segments,
each segment having a reinforcing section and an expanding section,
the plurality of segments coupled at their respective reinforcing sections via axial connecting sections which form nominal separation points for segmental length shortening,
at least one axial connecting section being a jigsaw-puzzle connecting section arranged between two adjacent reinforcing sections of two segments,
the jigsaw-puzzle connecting section being formed by at least one axially oriented recess in a first segment of the plurality of segments and at least one corresponding inserted section or axially oriented protrusion of a second segment of the plurality of segments that is adjacent to the first segment, the at least one corresponding inserted section or axially oriented protrusion fitted in the at least one axially oriented recess, the first and second segments each forming an axially acting undercut engagement by which the first and second segments are positively connected to one another in the axial direction and the circumferential/peripheral direction, but are configured to be separated by a radial relative movement of the first and second segments at the undercut engagement, wherein the expansion section has a plurality of spaced bands and the reinforcement section has a solid sheet structure.

19. The stent with retractor function according to claim 18, wherein the plurality of segments comprises a distal segment arranged at a distal end of the stent and having a first axial length, and one or more proximal segments located proximally to the distal segment, each of the one or more proximal segments having a second axial length, the first axial length being longer than the second axial length.

20. The stent with retractor function according to claim 18, wherein at least two connecting elements are formed on at least one of the plurality of segments, the at least two connecting elements diametrically opposed or evenly spaced in the circumferential/peripheral direction.

* * * * *